United States Patent
Divi et al.

(10) Patent No.: US 9,920,342 B2
(45) Date of Patent: Mar. 20, 2018

(54) PROCESS FOR THE PREPARATION OF DROXIDOPA

(71) Applicant: Divi's Laboratories Limited, Cyber Hills, Gachibowli, Hyderabad (IN)

(72) Inventors: Satchandra Kiran Divi, Hyderabad (IN); Mysore Aswatha Narayana Rao, Hyderabad (IN); Ponnekanti Purnachandra Rao, Hyderabad (IN); Shaik Nowshuddin, Hyderabad (IN)

(73) Assignee: Divi's Laboratories Limited

( * ) Notice: Subject to any disclaimer, the term of this patent is extended or adjusted under 35 U.S.C. 154(b) by 0 days.

(21) Appl. No.: 15/413,989

(22) Filed: Jan. 24, 2017

(65) Prior Publication Data

US 2017/0335357 A1 Nov. 23, 2017

(30) Foreign Application Priority Data

May 17, 2016 (IN) .............................. 201641017019

(51) Int. Cl.
  *C12P 13/00* (2006.01)
  *C07C 227/16* (2006.01)
(52) U.S. Cl.
  CPC .......... *C12P 13/001* (2013.01); *C07C 227/16* (2013.01); *C12Y 305/01014* (2013.01)
(58) Field of Classification Search
  None
  See application file for complete search history.

(56) References Cited

U.S. PATENT DOCUMENTS

| | | | |
|---|---|---|---|
| 4,480,109 A | 10/1984 | Ohashi et al. | |
| 4,562,263 A | 12/1985 | Ohashi et al. | |
| 4,699,879 A | 10/1987 | Umezawa et al. | |
| 2006/0166337 A1* | 7/2006 | Yamamoto | C12N 9/80 435/106 |
| 2013/0253061 A1 | 9/2013 | Pimplaskar et al. | |

FOREIGN PATENT DOCUMENTS

JP 2005204644 8/2005

OTHER PUBLICATIONS

Morishita et al. Tetrahedron Lett. (2015) 56: 6565-6568 (Year: 2015).*
Shiming Fan, et al., Biocatalytic Synthesis of Enantiopure B-Methoxy-B-arylalanine Derivatives, Eur. J. Org. Chem 2014, 5591-5597.
Tetsuya Tosa, et al., Studies on Continuous Enzyme Reactions, IV, Preparation of a DEAE-Sephadex-Aminoacylase Column and continuous Optical Resolution of Acyl-DL-Amino Acids, Biotechnology and Bioengineering, vol. IX, pp. 603-615(1967).
Tishkov, et al., Protein Engineering of Penicillin Acylase, Acta Naturae, vol. 2 No. 3(6) 2010.

* cited by examiner

*Primary Examiner* — Susan M Hanley
(74) *Attorney, Agent, or Firm* — Caesar Rivise, PC

(57) ABSTRACT

A novel process for the preparation of L-threo-dihydroxyphenylserine (Droxidopa) is described. It comprises of enantioselective hydrolysis of racemic (DL)-threo-N-acetyl-3-(3,4-methylenedioxyphenyl)-serine using commercially available L-amino acylase from *Aspergillus* sp. (EC 3.5.1.14) in the presence of cobalt ions, to obtain (L)-threo-3-(3,4-methylenedioxyphenyl)-serine followed by dealkylation to obtain Droxidopa. Protecting the amino group of (L)-threo-3-(3,4-methylenedioxyphenyl)-serine using either benzyloxycarbonyl or phthaloyl group before dealkylation followed by deprotection of the amino group results in obtaining Droxidopa in high yields and purity.

7 Claims, No Drawings

PROCESS FOR THE PREPARATION OF DROXIDOPA

FIELD OF INVENTION

The present invention relates to an improved enzymatic process for the preparation of L-threo-dihydroxy-phenyl serine, known as Droxidopa.

BACKGROUND OF THE INVENTION

Droxidopa is a prodrug of norepinephrine which by the action of dopa decarboxylase enzyme, is converted to norepinephrine in the body. It is used in the treatment of orthostatic hypotension. It is also useful in treating certain symptoms associated with Parkinson's disease. It is chemically (L)-threo-3-(3,4-methylenedioxyphenyl) serine (formula I) having the following structure:

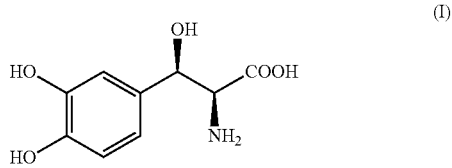 [SMILES: N[C@H](C(=O)O)[C@H](O)c1ccc(O)c(O)c1]

The U.S. Pat. No. 4,480,109 assigned to Sumitomo Chemical Company, Japan, describes a process for the preparation of Droxidopa (Scheme 1).

Scheme 1

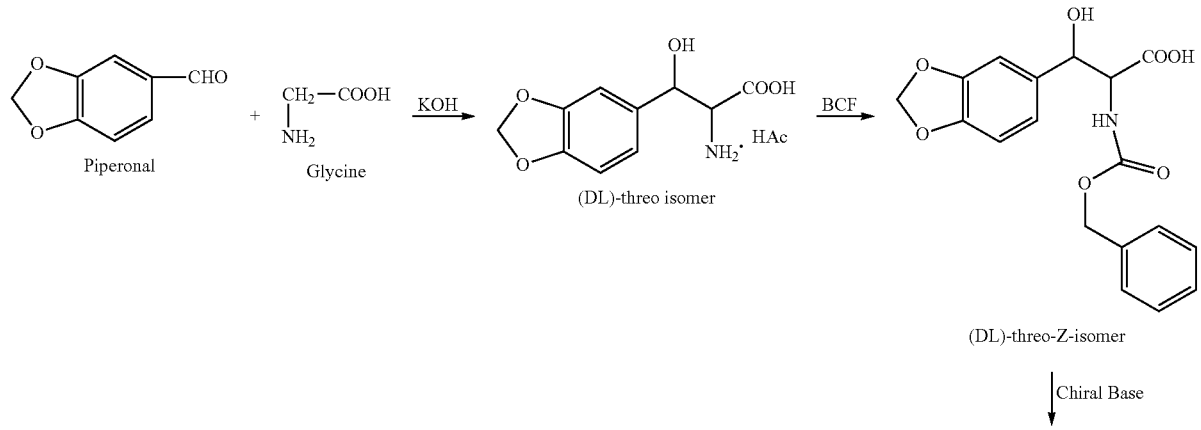

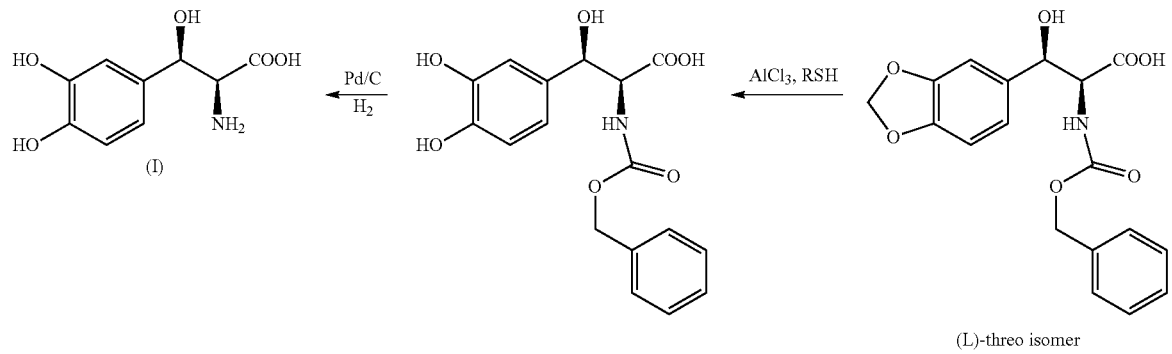

The scheme involves condensation of piperonal with glycine in the presence of a base to obtain (DL)-threo-3-(3,4-methylenedioxyphenyl)serine followed by N-protection by Schotten-Baumann reaction with benzyl chloroformate to give (DL)-threo-N-carbobenzyloxy-3-(3,4-methylenedioxyphenyl)serine. The racemic (DL)-threo isomer is resolved using chiral bases. The optically active (L)-threo-isomer obtained is reacted with Lewis acid, such as aluminum chloride, which releases the catechol moiety to obtain (L)-threo-N-carbobenzyloxy-3-(3,4-dihydroxyphenyl)serine. Addition of alkyl mercaptan improves the yield to a significant extent. Finally, carbobenzyloxy group is removed by catalytic hydrogenation to obtain Droxidopa (I).

A major drawback of the process is the resolution of the racemic (DL)-threo isomers to obtain the required (L)-threo isomer. The "109" patent describes the use of various resolving agents such as quinidine, quinine, ephedrine and (R)-amino diphenylpropanol. Although quinine gives the required (L)-isomer, it needs further crystallization to improve chiral purity. Quinine and ephedrine induce the precipitation of the salt of the unwanted (D)-isomer. Good resolution is obtained with (R)-aminodiphenyl propanol. However, the resolving agent is a synthetic chiral amine prepared from expensive D-alanine. The "109" patent also describes resolution of the (3,4-dihydroxyphenyl)serine, obtained after removing the methylene bridge using cinchonidine, brucine, ephedrine and (R)-aminodiphenyl propanol. However, the problems remains same. Resolution with brucine and ephedrine also results in the precipitation of D-isomer salt instead of the required (L)-isomer.

A slightly modified scheme was reported in U.S.2013/0253061 A1 (now abandoned), where the amino group is protected using phthaloyl group (Scheme 2)

Scheme 2

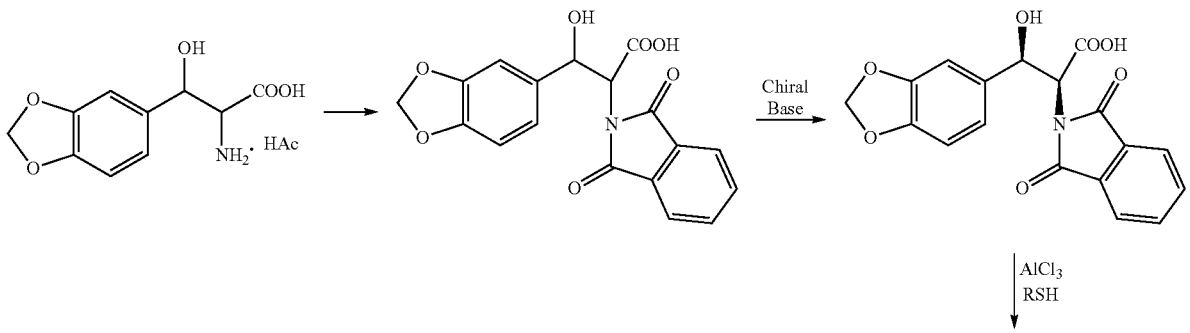

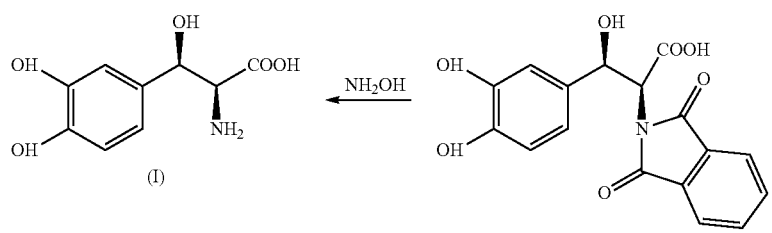

The scheme 2 also suffers from the same drawback as of the Scheme 1. Here, L-norephedrine is used as the chiral base in the resolution. L-norephedrine itself is a potent vasoconstrictor and its use is restricted in the USA as it increases the risk of stroke. Besides being expensive, the use of such a potent agent for the resolution is not advisable. Furthermore, seeding of the reaction mixture with pure (L)-threo isomer is required sometimes for obtaining the diasteromeric salt.

A Japanese application, JP2005204644 (A) (now abandoned) describes a process for the resolution of N-phenylacetyl-3-(3,4-methylenedioxyphenyl)serine using immobilized commercial penicillin G acylase from *E. coli* or *Arthrobacter viscosus* (Scheme 5):

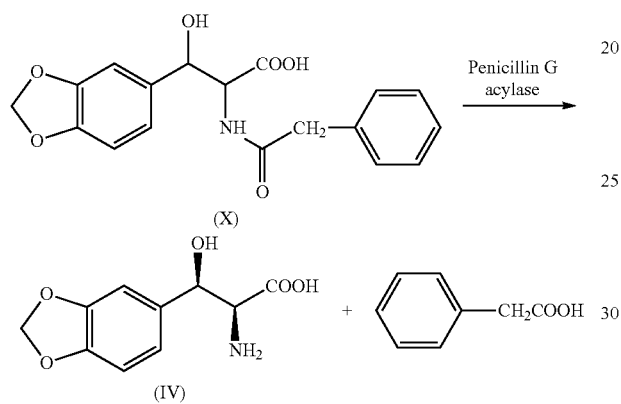

Penicillin G acylase is an enzyme used commercially to hydrolyse Penicillin G to obtain 6-aminopenicillanic acid (Scheme 6):

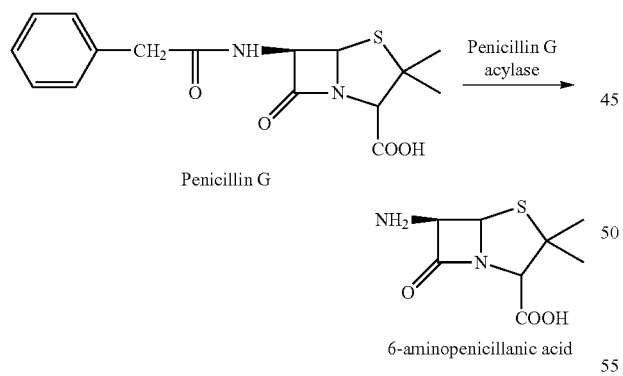

Penicillin G acylase only acts on N-phenylacetyl compounds indicating that an aromatic ring is essential for the activity. The substrate binding domain of the enzyme is hydrophobic, which makes it selective for phenyl or an aromatic ring (Tishkov et al, ActaNaturae, Vol. 2, No. 3 (6),2010, 47-61). Hence, the penicillin G acylase is not active on substrates with no aromatic ring on the acyl group, as in the case of (III) of the present invention.

Thus there is a need for better resolution methods for obtaining the required (L)-threo isomer from the racemic mixture.

SUMMARY OF THE INVENTION

The present invention describes a novel process to prepare Droxidopa which involves enzymatic resolution of using commercially available L-amino acylase from *Aspergillus* sp. (EC 3.5.1.14.; CAS No. 9012-37-7), in the presence of cobalt ions as given in the scheme 3:

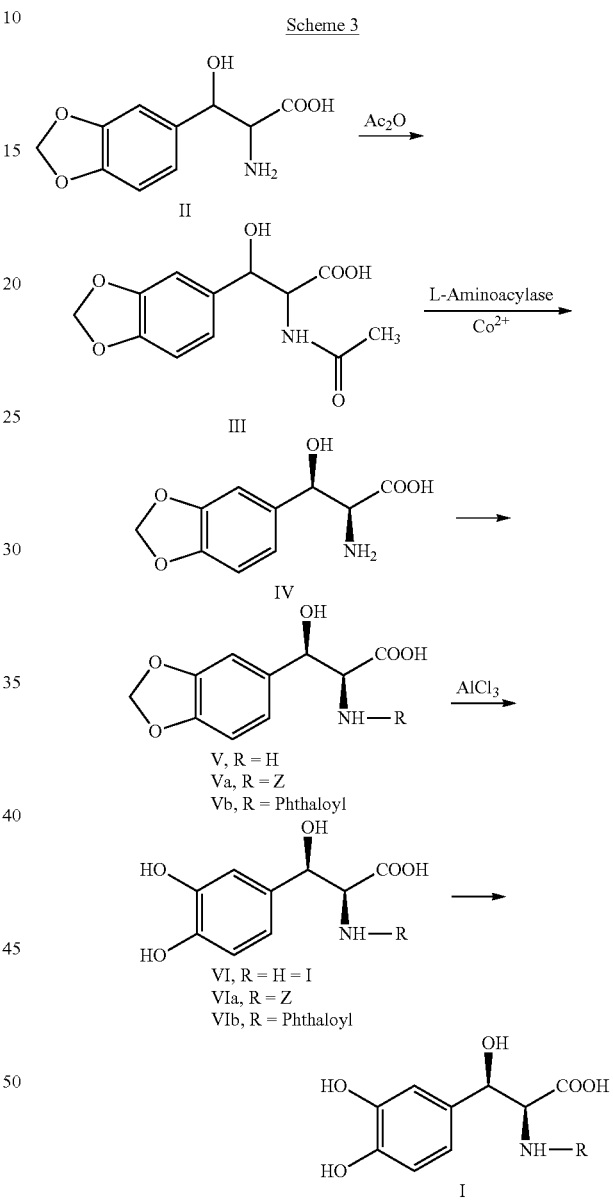

The process comprise sacetylation of (DL)-threo-3-(3,4-methylenedioxyphenyl)serine (II) to obtain (DL)-threo-N-acetyl-3-(3,4-methylenedioxyphenyl)serine (III), which is selectively hydrolysed by the L-amino acylase from *Aspergillus* sp. (EC 3.5.1.14), in the presence of cobalt ions, giving (L)-threo-3-(3,4-methylenedioxyphenyl)serine (IV)). Another aspect of the invention is the role of cobalt ions in catalyzing the enzyme reaction. In the absence of cobalt ions, the yields are very low.

Dealkylation of (IV) using aluminum chloride gives Droxidopa (I). However, it was found that when the amino group is protected with benzyloxycarbonyl (Va) or phthaloyl group (Vb), the dealkylation reaction is more efficient and gives higher yields of N-protected Droxidopa (VIa or VIb). Removal of the protecting group gives Droxidopa in good yields with high chemical and chiral purity.

DETAILED DESCRIPTION OF THE INVENTION

The present invention provides a novel process for the preparation of Droxidopa of formula I comprising the steps of:
(a) acetylation of (DL)-threo-3-(3,4-methylenedioxyphenyl) serine of formula II

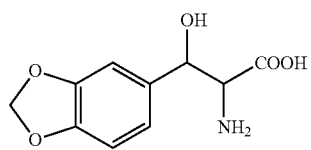
(II)

to produce (DL)-threo-N-acetyl-3-(3,4-methylenedioxyphenyl)serine of formula III,

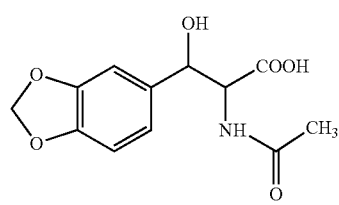
(VII)

(b) resolution of racemic (DL)-threo mixture of (III) using L-amino acylase from *Aspergillusspin* in the presence of cobalt ions to obtain (L)-threo-3-(3,4-methylenedioxyphenyl)serine of formula (IV) and

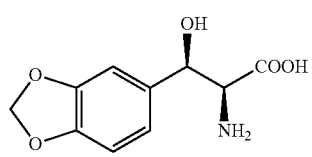
(IV)

(c) converting the (L)-threo isomer of formula (IV) to Droxidopa of formula (I)
(d) optionally protecting the amino group of (L)-threo isomer of formula (IV) with a protecting agent followed by demethylation and deprotection of the amino group to obtain Droxidopa of formula I

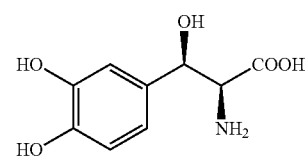
(I)

The required starting material, (DL)-threo-3-(3,4-methylenedioxyphenyl)serine of formula II, can be prepared by the method described in U.S. Pat. No. 4,480,109 or U.S.2013/0253061 A1. It is converted to (DL)-threo-N-acetyl-3-(3,4-methylenedioxyphenyl)serine of formula III using suitable acetylating agents such as acetic anhydride, acetyl chloride, acetyl ester or by reagents which generates-in situ anhydride or mixed anhydride of acetic acid or acetyl halide capable of acetylating the amino group of (II). Acetylation using acetic anhydride in an aqueous alkaline medium gives (III) in good yield and purity. Use of acetyl chloride as acetylating agent results in (III) with several impurities. Removals of these impurities is tedious and results in obtaining (III) in low yields.

The racemic (DL)-mixture (III) is resolved using L-amino acylase from *Aspergillus* sp. (EC 3.5.1.14) to obtain selectively (L)-threo-3-(3,4-methylenedioxyphenyl)serine of formula (IV) in excellent yields and chiral purity It is noteworthy for the present discussion that Umezawa et al, while describing a microbial resolution of racemic N-acyl-3-(3,4-dihydroxyphenyl)serine of the general formula (VII), where the phenolic group is protected,

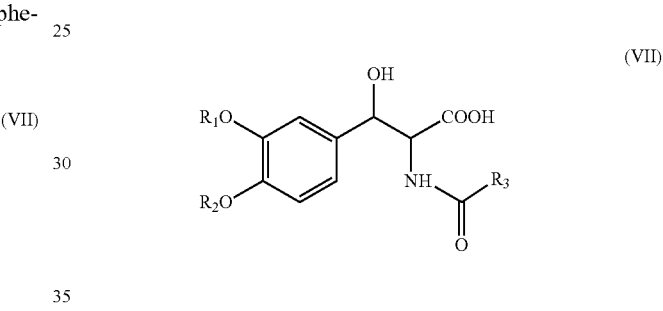
(VII)

mentions that: "As a result of our experiments, we have found that all the known acylases which are presently available are not capable of removing N-acyl group ($R^3CO$—) preferentially from the N-acetyl-L-3-(3,4-dihydroxyphenyl)serine by asymmetrical hydrolysis." (U.S. Pat. No. 4,699,879, column 2, line 65). Umezawa describes a microbial method using a microorganism selected from the group consisting of *Actinomycesaureoverticillatus* ATCC 19726, *Actinomyces bicolor* ATCC 23614, *Streptomyces blastomyceticus* ATCC 19731, *Streptomyces chartreusis* ATCC 19738,*Streptomyces flavopersicus* ATCC 19756, *Actinomycesflavotricini* ATCC 23621, *Streptoverticillumgriseocameum* ATCC 19763, *Streptomyces hachijoensis* ATCC 19769,*Streptomyces halstedii* ATCC 19770, *Streptoverticillumhiroshimense* ATCC 19772, *Streptomyces tenadae* ATCC 19812 and *Streptomyces toyocaensis* ATCC 19814 or the extracts of the said microorganisms, for the resolution of racemic phenolicgroupprotected derivative of N-acyl-3-(3,4-dihydroxyphenyl)serine of the general formula (VII). Umezawa does not mention *Aspergillus* species, which is the source of the enzyme used in the present invention.

Shiming Fan et al (*Eur. J. Org. Chem.* 2014, 5591-5597) studied the resolution of racemic mixture of N-acetyl-β-hydroxy-β-phenylalanine (VIII) using both L-amino acylase and D-amino acylase (Scheme 4):

Scheme 4

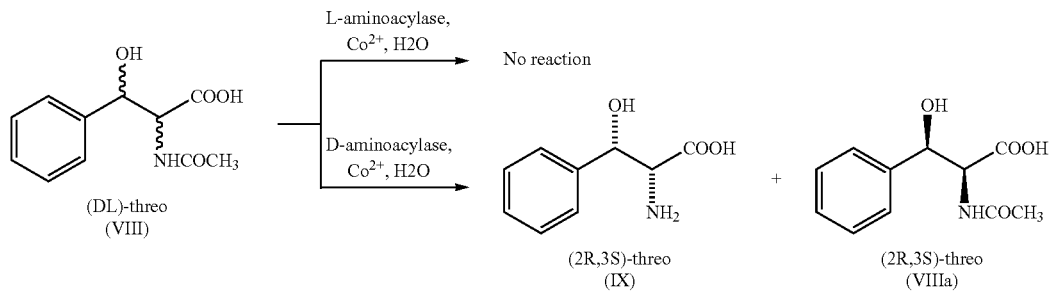

The L-amino acylase from *Aspergillus oryzae* (EC 3.5.1.4; Sigma-Aldrich) was unable to hydrolyse the N-acetyl group in (DL)-threo isomer (VIII). The D-amino acylase from recombinant *Escherichia coli* (EC 3.5.1.81) hydrolyzed (VIII) to give (2R, 3S)-threo isomer (IX). But, the (2S, 3R)-threo isomer (VIIIa), whose stereochemistry is similar to that in Droxidopa, could not be hydrolyzed. Results were similar when the phenyl ring was substituted with chloro, methoxy or hydroxyl group at 4-position. Shiming Fan et al concluded that L-amino acylase (EC 3.5.1.4) was not active against (DL)-threo-3-phenylserine derivatives.

Thus the prior art literature strongly dissuades one from exploring a simple N-acetyl derivative for developing an enzymatic process using amino acylase for the preparation of Droxidopa. However, our efforts have resulted in developing an efficient process for this.

In the present invention, the enzymatic reaction of the enantioselective hydrolysis can be carried out in an aqueous medium over wide ranges of pH and temperature. To dissolve the substrate, a polar solvent such as methanol, ethanol, acetonitrile or tetrahydrofuran may be employed at a ratio which will not affect the enzyme reaction. The substrate (III) has good solubility in water and gives a clear solution. The reaction may be carried out at a pH of about 5.0 to 8.5, but typically at about 6.0 to 7.5. It is necessary to control the pH during the reaction because of the liberation of acetic acid, which decreases the pH of the medium. The pH can be controlled by the addition of alkali either manually or by pH Stat. The pH can also be controlled internally by using suitable buffer.

The reaction may be carried out at a temperature range of 15° C. to 55° C., typically at room temperature of about 25° C. Higher yields were obtained when the reaction is carried out at about 40° C. to 45° C.

Another important aspect of the present invention is the catalytic effect of cobalt ions on the enzymatic enantioselective hydrolysis of (III) to (IV). Cobalt ions are known to activate the amino acylase enzyme (Tosa T et al, Biotechnology & Bioengineering, Volume IX, 603-615, 1967). Addition of cobalt salt such as cobalt chloride significantly increased the yields and the chiral purity of the product (IV). Optimum yields are obtained when about 0.004 mol equivalents of cobalt chloride is used.

Variation of the enzyme concentration showed that 1.5% weight by weight to the substrate concentration (Enzyme activity=>30,000 unit/g) is sufficient to obtain optimum yields.

It is also interesting that the acylase enzyme was inactive on N-acetyl derivative of (DL) Droxidopa suggesting that the reaction will not take place when the phenolic group is free.

The cleavage of methylenedioxy moiety is generally achieved by the reaction with a Lewis acid such as aluminum halide, ferric chloride, stannic chloride, boron trichloride, boron tribromide, etc. together with alkyl mercaptan. The conversion of (IV) to Droxidopa (I) using aluminum halide and alkyl mercaptan can be carried out as described in U.S. Pat. No. 4,480,109 (Example 4) or in JP2005204644 (A).

Although, the methylene dioxy moiety of (IV) can be directly cleaved as described above, isolation of pure Droxidopa is tedious because of the presence of aluminum salts and high polarity of the compound. This problem can be solved by protecting the amino group with benzyloxycarbonyl (Va) or with phthaloyl group (Vb). However, Boc group is not useful as protecting group as it gets cleaved during the dealkylation stage. Both Va and Vb underwent dealkylation smoothly. Because of its non-polar nature, VIa and VIb can be easily isolated in pure form by extracting the aqueous reaction mixture with an organic solvent. The benzyloxy carbonyl group can be removed by catalytic hydrogenation to obtain Droxidopa in high yields and in pure form. The phthaloyl group can be removed using either hydrazine hydrate as described in U.S. Pat. No. 4,562,263 or using hydroxylamine as reported in U.S.2013/0253061A1 to obtain Droxidopa in high yields and in pure form.

The embodiments of the present invention are illustrated in the following examples, which are not intended in any way to limit the scope of the invention. One skilled in the art can modify the details to suit the inputs and desired outcomes without affecting the present invention.

EXAMPLES

Chemical purity was determined using HPLC under the following conditions:

Column: X Terra RP18, 150×4.6 mm, 3.5 µm

Mobile phase: Buffer:Acetonitrile (93:7)

Buffer Preparation: Sodium 1-heptane sulfonate (1.0)g and potassium phosphate (1.36 g) are dissolved in 1000 ml of $H_2O$ and pH of the buffer is maintained at 2.0 using phosphoric acid Diluent: 0.1M Hydrochloric acid solution Injection Volume: 20 µl flow rate: 1.0 ml/min Detection: 220 nm Temperature: 27° C.
Run Time: 35 min
Enantiomeric purity was determined using HPLC under the following conditions:
Column: Crownpack CR+, 150×4 0 mm, 5 μm
Mobile phase: Taken 16.3 g of 70% perchloric acid in 1000 ml of water (maintained pH at 1.0)
Diluent: Water
flow rate: 0.4 ml/min
Temperature: 15° C.
Detection: 200 nm
Enzyme: L-aminoacylase from *Aspergillus* sp. (EC 3.5.1.14.; CAS No. 9012-37-7) having the activity of >30,000 u/g was purchased from Amano Enzyme Inc. (Nagoya, Japan).
Cobalt chloride hexahydrate, ACS reagent (98%) from Sigma-Aldrich was used in the enzyme reaction Example-1

Preparation of DL-threo-3-(3,4-methylenedioxyphenyl)serine (II)

Potassium hydroxide (8.5 g) was added to methanol (41.5 mL) and stirred for 30 min at 25-30° C. to obtain a clear solution. To this was added glycine (5.2 g, 0.069 mole) and toluene (31.0 mL) while stirring. Piperonal (22.9 g, 0.15 mole) was dissolved in toluene (31.0 mL) and was added to the above reaction mixture and stirred for 18 hrs at RT. The reaction temperature was increased to 40° C. and the solvents (toluene and methanol) were distilled off under vacuum until mixture becomes thick. Additional toluene (21.0 mL) was added to the reaction mass three times and distilled out for complete removal of methanol and toluene. The reaction mixture was kept under vacuum at 40° C. After 3 hrs, the reaction mixture was cooled to 18-22° C., dilute hydrochloric acid (23.0 mL) and 114.5 mL water added and stirred for 30 min.

The mixture was allowed to settle for 30 min to separate into organic and aqueous layers. The aqueous layer was collected and washed with toluene (31.0 mL). Glacial acetic acid (21.8 g) was added to the aqueous layer. The reaction mass pH was adjusted to 5.4 to 5.5 with 30% sodium hydroxide solution at 25-30° C. The product was filtered and the resulting wet cake was washed with water (5.0 mL). The cake was dried at 50-55° C. under vacuum to get DL-threo-3-(3,4-methylenedioxyphenyl)serine (II) (Yield: 14.5 g, 93%, HPLC: 99.7%, Melting point: 189-191° C.)

Example-2

Preparation of DL-threo-N-acetyl-3-(3,4-methylenedioxyphenyl)serine (III)

Threo-3-(3,4-methylenedioxyphenyl)serine (II), (50.0.g, 0.22 mole) was added, lot wise, to a solution of sodium hydroxide (26.0 g, 0.66 mole) in 500.0 mL water to get a clear solution at room temperature. To the above reaction mass, acetic anhydride (29.49 g, 0.289 mole) was added slowly and stirred overnight at R.T. After cooling to 0-5° C., the pH was adjusted to about 1.5 with HCl, and stirred for one hour. The white solid obtained was collected by filtration, and dried under vacuum to give (III) (Yield: 50.4 g, 85%; Melting point: 199-200° C.; HPLC, 99.6%); IR (KBr): 3298.66, 3075, 2949.42, 2912.58, 2837.15, 1863.19, 1744.96, 1724.00, 1642.50, 1558.92, 1504.83, 1446.43, 1285.63, 1220.46, 1140.97, 1039.91, 880.24 Cm$^{-1}$; $^1$HNMR (300 MHz DMSO): δ 1.77(s, 3H), δ 4.38 (m, 1H), δ 5.05 (d, 1H), δ5.97 (t, 2H) δ 6.7-6.9 (m, 3H) δ8.00 (d, 1H); $^{13}$C NMR (300 MHz, DMSO): 174.7, 170.7, 149.7, 147.2, 134.6, 120.0, 109.2, 108.2, 101.3 70.8, 68.3, 23.3, m/z (M+1): 268.4

Example-3

Preparation of L-threo-3-(3,4-methylenedioxyphenyl)serine (IV)

DL-threo-N-acetyl-3-(3, 4-methylenedioxyphenyl)serine (III) (25.0 g, 0.093 mole) and cobalt chloride hexahydrate (0.089 g, 0.004 mole) were dissolved in 250.0 mL of water. To the solution, L-amino acylase from *Aspergillus* sp (0.75 g) was added, and the pH adjusted to 7.5 using 20% NaOH solution. The reaction mass was warmed to 40-45° C. and stirred overnight at pH 7.5. Reaction mass was cooled to 0-5° C. and the pH was adjusted to ~1 with HCl, stirred for 10 to 20 min which results in the precipitation of the unwanted isomer. After removing the unwanted isomer by filtration, the filtrate was collected and was saturated with powdered NaCl. The saturated solution was washed with ethyl acetate to remove non polar impurities. The aqueous layer was extracted with n-BuOH. Solvent was removed under vacuum to get white solid of (IV) (yield: 9.45 g; 45%; Melting point: 195-196° C.; chemical purity: 99.7%, chiral purity 99.8%). IR (KBr): 3284.62, 2959.72, 2918.12, 2784.21, 1603.81, 1504.42, 1490.45, 1446.90, 1412.24, 1255.66, 1124.86, 1097.45, 1040.02, 933.04, 811.37 Cm$^{-1}$; 1HNMR(300 MHz, DMSO); δ 3.24(d, 1H), δ 4.75 (d, 1H), δ 5.95 (s, 2H), 6.80(s, 2H), δ 6.91 (s, 1H), $^{13}$C NMR (300 MHz, DMSO) 174.7, 149.7, 147.5, 134.5, 120.3, 109.6, 108.8, 73.6, 67.3: m/z (M+1): 226.1

Example-4

Preparation of L-threo-3-(3, 4-methylenedioxyphenyl)serine(IV)

The reaction was conducted as described in Example-3, except that the enzyme reaction was conducted at a temperature of 25° C. instead of 45° C. Only 30% conversion was observed and the isolated product contained some D-isomer. Yield: 6.3 g, 30%, chiral purity 88%.

Example-5

Preparation of L-threo-3-(3,4-methylenedioxyphenyl)serine(IV)

The reaction was conducted as described in Example-3, except that the enzyme reaction was conducted at a pH of 6.5 instead of 7.5. Yield: 5.67 g, 27%, chiral purity 97%.

Example-6

Preparation of L-threo-3-(3,4-methylenedioxyphenyl)serine(IV)

The reaction was conducted as described in Example-3, except that the enzyme reaction was conducted using cobalt chloride at a concentration of 0.04 g, 0.002 mole instead of 0.08 g 0.004 mole. Yield: 6.93 g 33%, chiral purity 90.0%.

Example-7

Preparation of Droxidopa (I)

Anhydrous aluminum trichloride powder (2.03 g 0.015 mole) was added to 50.0 mL of anhydrous dichloromethane at 0-5° C. under nitrogen atmosphere. To the stirred reaction mass added 3.05 g (0.015 mole) of 1-dodecanthiol. After 15-minute stirring the resultant yellowish solution, 1.08 g (0.0048 mole) of L-threo-3-(3,4-methylenedioxyphenyl)serine (IV) was added. After 2 hrs, 25.0 mL methanol was added resulting in an exothermic reaction which was controlled by keeping the temperature less than 10° C. The reaction mass was concentrated under reduced pressure resulting in an oil to which was added 30.0 mL water. After addition of 3N HCl to pH 2.0, the aqueous solution was washed with Ethyl acetate to remove the remaining mercaptan. To the aqueous solution was added sodium acetate trihydrate which resulted in the precipitation of Droxidopa. After drying, Droxidopa, (yield, 0.51 g 49.8%), chemical purity: 99.5%, Chiral purity: 99.6% was obtained. Melting point: 224-225° C.; optical rotation: $[\alpha]^{20}_D=-39.9°$ (c=1 in HCl 1M). IR (KBr): 3440.49, 3221.15, 3034.78, 2918.41, 2853.35, 2609.13, 1663.73, 1591.50, 1523.01, 1452.37, 1407.00, 1351.26, 1288.74, 1228.91, 1124.05, 1014.98, 925.58, 824 $Cm^{-1}$: $^1$H NMR (300 MHz, $D_2O$): δ 4.1 (s, 1H), δ 5.1 (s, 1H), δ 6.7-6.8 (m, 3H); $^{13}$C NMR(300 MHz, $D_2O$ δ 58.91, 70.04, 113.65, 116.40, 118.39, 130.35, 144.17, 169.62: m/z (M+1):213.9

Example-8

Preparation of L-threo-N-benzyloxycarbonyl-3-(3,4-methylenedioxyphenyl) serine (Va)

L-threo-3-(3,4-methylenedioxyphenyl)serine(IV) (10.0 g, 0.044 mole) was added to 100.0 mL water, followed by sodium hydroxide (2.6 g, 0.066 mole) at 0-5° C. To the above solution was added 50% solution of benzyl chloroformate (16.6 g, 0.0486 mole) dropwise at 0-5° C. Maintained The reaction mass was at pH 8.5 to 9.0 with 30% sodium hydroxide solution and stirred for 1 hr at 0-5° C. The reaction mass was cooled to room temperature and stirred overnight. The toluene layer was separated and the aqueous layer was washed with n-hexanes to remove excess benzyl chloroformate. The pH of the solution was adjusted to 0.5 to 1.0 using HCl and was extracted the product with ethyl acetate. The organic layer was dried over $Na_2SO_4$, solvent evaporated under vacuum to get an oily crude of (Va) (yield 13.5 g, 85%, HPLC: 98%)

Example-9

Preparation of L-threo-N-benzyloxycarbonyl-3-(3,4-dihydroxyphenyl)serine (VIa)

The oily crude of (Va) (2.5 g, 0.0347 mole), obtained from Experiment-8 was dissolved in dichloromethane (350.0 mL) at room temperature under nitrogen atmosphere. To this solution was added 1-octanethiol (29.68 g, 0.2 mole) and cooled to 0-5° C. Aluminum chloride (14.0 g, 0.105 mole) was added and stirred at 0-5° C. for 5 hrs. The reaction mass was cooled to −10° C. and 10% solution of oxalic acid (120.0 mL) was added dropwise for 20-30 min. The dichloromethane layer was separated and the aqueous layer was washed with n-hexanes for the removal of excess 1-octanethiol. The aqueous layer was extracted with ethylacetate. The organic layer was treated with 10% sodium bicarbonate solution (120.0 mL). The aqueous bicarbonate layer was collected and its pH was adjusted to 1.0 using HCl at 0-5° C. The solution was extracted with ethyl acetate. The ethyl acetate layer was dried over $Na_2SO_4$, and concentrated under vacuum to get gummy solid (VIa) (yield 6.1 g, 50%, HPLC: 96%)

Example-10

Preparation of Droxidopa (I)

L-threo-N-benzyloxycarbonyl-3-(3,4-dihydroxyphenyl)serine (VIa), obtained from example-9 (5.5 g, 0.0158 mole) was dissolved in methanol (50.0 mL) in SS hydrogenation flask at room temperature. Water, 5.5 mL, acetic acid, 0.2 mL, and 10% Pd/C (1.0 g) were added and hydrogenated for 4 hr. To the reaction mass was added 2.0 mL HCl and filtered through hyflow. The filtrate was collected and its pH was adjusted to 6.5-7.0 using methanolic solution of triethyl amine Ash colored solid obtained was filtered and washed with acetone (20.0 mL). The solid was dissolved in dilute HCl and stirred to get white hydrochloride salt. The salt was treated with a solution of triethylamine in methanol resulting in the precipitation of Droxidopa as white solid, yield 1.9 g, 56%, Melting point: 225-226° C., chemical purity: 99.8%, chiral purity: 99.9%, optical rotation range: $[\alpha]^{20}_D=-39.9°$ (c=1 in HCl 1M).

Example-11

Preparation of L-threo-N-Phthaloyl-3-(3,4-methylenedioxyphenyl)serine(Vb)

To a solution of sodium carbonate (2.55 g, 0.024 mole) in 50.0 mL water was added L-threo-3-(3,4-methylenedioxyphenyl)serine (IV) (5.0 g, 0.02 mole) slowly at 0-5° C. N-carbethoxy phthalimide (5.83 g, 0.028 mole) was added to above reaction mixture slowly. The reaction mixture was allowed to reach room temperature and then stirred for 5 hrs. Cooled the reaction mixture to 0 to 5° C. and adjusted the pH to about 1.0 with HCl. White solid obtained was filtered, and the solid was dried for 2 hrs at room temperature to obtain Vb (yield 7.1 g, 90%, Melting point: 120-123° C., HPLC 98.2%)

Example-12

Preparation of L-threo-N-Phthaloyl-3-(3,4-dihydroxyphenyl)serine (VIb)

L-threo-N-Phthaloyl-3-(3,4-methylenedioxyphenyl)serine (Vb) obtained from example-11 (5.5 g, 0.015 mole) was dissolved in dichloromethane (100.0 mL) at room temperature under nitrogen atmosphere. To the above solution was added 1-octanethiol (16.3 g, 0.111 mole), cooled to −10° C. Aluminum chloride (12.13 g, 0.091 mole) was added lot wise (3 lots). The reaction mixture was stirred for 2 hrs at −10° C. and 2 hr at 10-15° C. Excess aluminum chloride was decomposed by adding oxalic acid solution (5.5 g oxalic acid dissolved in 100 ml water) at −10° C. The reaction mixture was heated to remove the dichloromethane. The cooled aqueous layer was washed with n-hexanes (25.0 mL×2) to remove excess 1-octanethiol. The product was extracted from the aqueous solution with ethyl acetate (50 mL×2). The ethyl acetate layer was concentrated under vacuum to get foamy solid of VIb. (yield, 3.75 g, 70.62%, HPLC: 97.6%)

Example-13

Preparation of Droxidopa (I)

To an aqueous solution of sodium bicarbonate (1.4 g, 0.016 mole, in 19.0 mL water) was added 30.0 mL methanol and hydroxylamine hydrochloride (1.17 g, 0.016 mole). To this was added a solution of L-threo-N-phthaloyl-3-(3,4-dihydroxyphenyl)serine (VIb) (3.7 g, 0.01 mole), obtained from example-12, dissolved in 40.0 mL methanol. The reaction mixture was heated and refluxed for 12 hrs. On cooling and stirring for one hour at 20-25° C. results in the precipitation of off-white solid. After filtering, the solid was collected and dissolved in dilute HCl and stirred to get white hydrochloride salt of Droxidopa. The salt was neutralized using triethylamine in methanol to get white solid of Droxidopa. (yield 1.38 g, 60%, HPLC: 99.8%, Chiral 100%), Melting point: 224-225° C.; optical rotation range: $[\alpha]^{20}_D = -40.1°$ (c=1 in HCl 1M).

We claim:

1. A process for the preparation of (L)-threo-3-(3,4-methylenedioxyphenyl)serine (Droxidopa) comprising:

a) acetylation of (DL)-threo-3-(3,4-methylenedioxyphenyl)serine of formula II with an acetylating agent

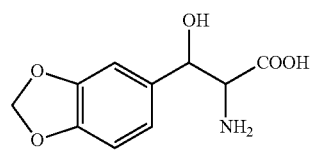

to obtain (DL)-threo-N-acetyl-3-(3,4-methylenedioxyphenyl)serine of the formula III, followed by

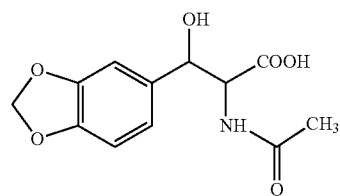

(b) enantioselective hydrolysis of racemic (DL)-threo compound of the formula (III) using L-aminoacylase from *Aspergillus* sp.(EC 3.5.1.14) in the presence of cobalt ionstoobtain(L)-threo-3-(3,4-methylenedioxyphenyl)-serine of formula (IV) and

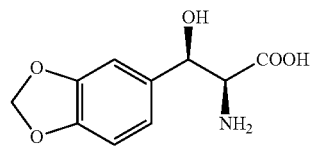

(c) converting (L)-threo isomer of formula (IV) to Droxidopa of formula (I)

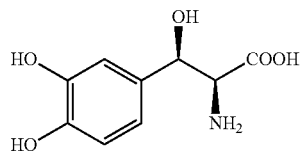

(d) optionally protecting the amino group of (L)-threo isomer of formula (IV) with a protecting agent followed by demethylation and deprotection of the amino group to obtain Droxidopa of formula I.

2. A process according to claim 1 (a), wherein the acetylation is carried out using acetic anhydride.

3. A process according to claim 1 (b), wherein the hydrolysis is carried out at a temperature between 15° C. to 55° C.

4. A process according to claim 1 (b), wherein the hydrolysis is carried out at a pH of 5 to 8.5.

5. A process according to claim 1 (b),wherein the hydrolysis is carried out in the presence of cobalt ions where the ratio between cobalt ions and the substrate (DL)-threo compound of the formula (III) is 0.002: 1.0 to 0.11: 1.0.

6. A process according to claim 1 (d), wherein the (L)-threo isomer of formula (IV) is converted to Droxidopa of formula (I), by first converting(IV) to its N-benzyloxy carbonyl derivative of the formula (Va);

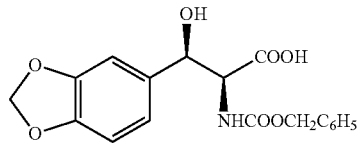

converting (Va) to a compound of the formula (VIa) and

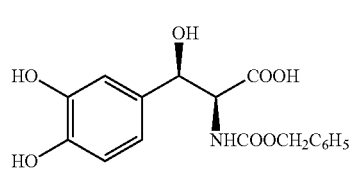

converting the compound of the formula (VIa) to(I).

7. A process according to claim 1 (d), wherein the (L)-threo isomer of formula (IV) is converted to Droxidopa of formula (I), by first converting IV to its N-phthaloyl derivative of the formula (Vb) and

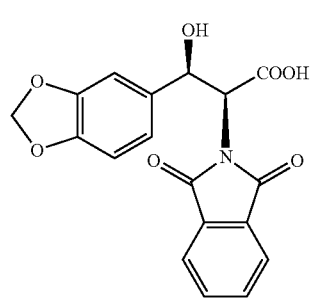
(Vb)
converting (Vb) to a compound of the formula (VIb) and
(VIb)
converting the compound of the formula (VIb) to (I).
* * * * *